US009897606B2

(12) United States Patent
Li et al.

(10) Patent No.: US 9,897,606 B2
(45) Date of Patent: Feb. 20, 2018

(54) REAGENTS AND METHODS FOR DETECTING INFLUENZA

(71) Applicant: Her Majesty the Queen in Right of Canada as represented by the Minister of Health, Winnipeg (CA)

(72) Inventors: Xuguang Li, Winnipeg (CA); Runtao He, Winnipeg (CA); Gary Van Domselaar, Winnipeg (CA)

( * ) Notice: Subject to any disclaimer, the term of this patent is extended or adjusted under 35 U.S.C. 154(b) by 0 days.

(21) Appl. No.: 15/219,976

(22) Filed: Jul. 26, 2016

(65) Prior Publication Data

US 2017/0131277 A1    May 11, 2017

Related U.S. Application Data

(62) Division of application No. 14/556,415, filed on Dec. 1, 2014, now Pat. No. 9,427,462, which is a division of application No. 13/322,459, filed as application No. PCT/CA2010/000784 on Jun. 1, 2009, now Pat. No. 8,926,982.

(60) Provisional application No. 61/182,920, filed on Jun. 1, 2009.

(51) Int. Cl.
*A61K 45/06* (2006.01)
*G01N 33/569* (2006.01)
*C12N 9/24* (2006.01)

(52) U.S. Cl.
CPC ..... *G01N 33/56983* (2013.01); *C12N 9/2402* (2013.01); *C12Y 302/01018* (2013.01); *G01N 2333/924* (2013.01)

(58) Field of Classification Search
None
See application file for complete search history.

(56) References Cited

U.S. PATENT DOCUMENTS

| 4,459,286 A * | 7/1984 | Hilleman | A61K 39/095 424/164.1 |
| 2005/0002948 A1 * | 1/2005 | Ryall | A61K 39/02 424/184.1 |

FOREIGN PATENT DOCUMENTS

| WO | WO2002/072627 A2 * | 9/2002 | C07K 14/47 |
| WO | WO2008/039267 A2 * | 4/2008 | C07H 21/02 |

* cited by examiner

*Primary Examiner* — Agnieszka Boesen
(74) *Attorney, Agent, or Firm* — Michael R. Williams; Ryan W. Dupuis; Ade & Company Inc.

(57) ABSTRACT

Two universally conserved sequences from influenza type A neuraminidases were identified by large scale sequence analysis then chemically modified and conjugated to carrier proteins to generate mono-specific and monoclonal antibodies. The two antibodies, one targeting the N-terminus of the type A neuraminidase and the other sequence close to enzymatic active site, were capable of binding to all 9 subtypes of neuraminidase while demonstrating remarkable specificity against the viral neuraminidase sequences since no cross-reactivity against allantoic proteins was observed. Quantitative analyses of NA using slot blot suggest that the antibodies can be used for NA antigen quantitation in vaccines. These represent the first time the antibody-based immunoassay can be used for NA quantitative determination.

7 Claims, 6 Drawing Sheets

REAGENTS AND METHODS FOR DETECTING INFLUENZA

This application is a divisional application of U.S. Ser. No. 14/556,415, filed Dec. 1, 2014 which was a divisional application of U.S. Ser. No. 13/322,459, filed Nov. 24, 2011 which was a 371 of PCT Application CA10/00784, filed May 28, 2010, now abandoned, which claimed the benefit of U.S. Provisional Patent Application U.S. Ser. No. 61/182,920 filed on Jun. 1, 2009.

FIELD OF THE INVENTION

The present invention relates to reagents and methods for detecting influenza virus proteins, in particular neuraminidase (NA). In particular, the present invention relates to peptide conjugates, antibodies, and use of antibodies for detecting neuraminidase in a sample, especially for verifying potency of influenza vaccines.

BACKGROUND OF THE INVENTION

Influenza can infect as much as 5-15% of the world population, resulting in 3-5 million cases of severe illness and up to 500,000 deaths each year. In the U.S. alone, flu epidemics lead to approximately 300,000 influenza-related hospital admissions and 36,000 influenza-related deaths annually in addition to an estimated cost of $12 billion per year (Poland 2001; Simonsen et al. 2007, PMID: 17897608). Current seasonal influenza vaccines are produced with strains recommended by the World Health Organization about 9-12 months ahead of the targeted season (Carrat et al. 2007). The vaccines typically contain two type A influenza strains and one type B strain, which are predicted to be the most likely strains to cause the upcoming flu epidemic.

However, there are inherent disadvantages associated with the preparation of conventional influenza vaccines such as the uncertainty of the actual circulating strain, the need for annual updating of the manufacturing process and preparation of reagents for vaccine lot release. Furthermore, mismatches between the strains selected for vaccine preparation and the circulating viruses were found to be responsible for much reduced efficacy of the seasonal influenza vaccines (Bridges et al. 2000; De Filette et al. 2005). Clearly, the drawbacks associated with traditional vaccine preparation would be drastically exacerbated in the event of an outbreak of pandemic influenza, given a perceivably much shortened timeframe available for the production of prophylactic vaccines for global needs. All these problems concerning the influenza vaccines are largely due to one single biological property of the influenza virus itself, i.e. the constant mutations of the virus surface proteins hemagglutinin (HA) and neuraminidase (NA).

Currently, influenza A viruses representing 16 HA and 9 NA subtypes have been detected in wild birds and poultry throughout the world (Zambon 1999; Treanor 2004; Fouchier 2005). Frequent antigenic drifting or shifting of HA and NA prompted numerous exploratory investigations of vaccines that are intended to induce host immune responses against viral proteins that are less subject to antigenic fluctuations. Of these conserved antigenic determinants, the nucleoproteins (NP) and Matrix (M) have been shown to induce protective immunity against diverse strains of the viruses (Frace et al. 1999; Epstein et al. 2002; de Filette 2005; Mozdzanowska et al. 2003; Fan et al. 2004). Furthermore, it has been suggested that cell-mediated immune response rather than humoral immune responses protect the animals immunized with NP-based vaccines while antibody-mediated protections against lethal challenges of various subtypes of influenza virus were reported with the use of M2-based vaccines (Neirynck et al. 1999; de Filette et al 2005; Mozdzanowska et al. 2003). None of these universal vaccines appears to prevent viral infection in animal studies although prevention of clinical diseases was found to be promising (Gerhard et al. 2006).

Given the importance of neutralizing antibodies against NA in preventing influenza infection, the conserved regions in the NA proteins have also received great attention in recent years.

There remains a need in the art for reagents that may be universally used to detect influenza viruses or proteins therein, especially neuraminidase (NA) proteins.

SUMMARY OF THE INVENTION

According to a first aspect of the invention, there is provided a composition comprising an influenza neuraminidase peptide consisting of the amino acid sequence as set forth in SEQ ID No. 1 or SEQ ID No. 2 attached to a first end of a spacer, said spacer being attached at a second end thereof to a carrier protein.

According to a second aspect of the invention, there is provided a composition comprising an influenza neuraminidase peptide consisting of the amino acid sequence as set forth in SEQ ID No. 1 or SEQ ID No. 2 attached to a first end of a spacer, said spacer being attached at a second end thereof to a first end of a linker, said linker being attached at a second end thereof to a carrier protein.

According to a third aspect of the invention, there is provided a method of inducing an immune response in an individual in need of or desirous of such treatment comprising administering to said individual an effective amount of the composition as described above.

According to a fourth aspect of the invention, there is provided a method of preparing antibodies against influenza virus neuraminidase comprising inoculating an animal with an effective amount of the composition as described above and after the animal has produced antibodies against said composition, recovering said antibodies from said animal.

According to a fifth aspect of the invention, there is provided a method of preparing monoclonal antibodies against influenza virus neuraminidase comprising inoculating an animal with an effective amount of the composition as described above, removing antibody-producing cells from said animal, fusing a respective one of said antibody-producing cells with a respective one of an immortal cell line, thereby producing a respective one hybridoma cell, and selecting for hybridoma cells producing antibodies against said composition.

According to a sixth aspect of the invention, there is provided a method of determining the potency of an influenza vaccine preparation comprising providing an influenza vaccine preparation to be tested and determining the amount of neuraminidase in said vaccine preparation using antibodies prepared according to one of the methods described above, wherein higher levels of neuraminidase are indicative of a more potent vaccine preparation.

BRIEF DESCRIPTION OF THE DRAWINGS

FIG. 1 represents the highly conserved epitope designated HCA-2, near the enzymatically active site of all NA enzymes. For the NA of /A/California/07/2009, the epitope is located at amino acid positions from 221-230 (N2 numbering).

FIG. 2 represents the universally conserved epitope designated HCA-3, at the N-terminus of all NA type A enzymes.

DESCRIPTION OF THE PREFERRED EMBODIMENTS

Figure 1:
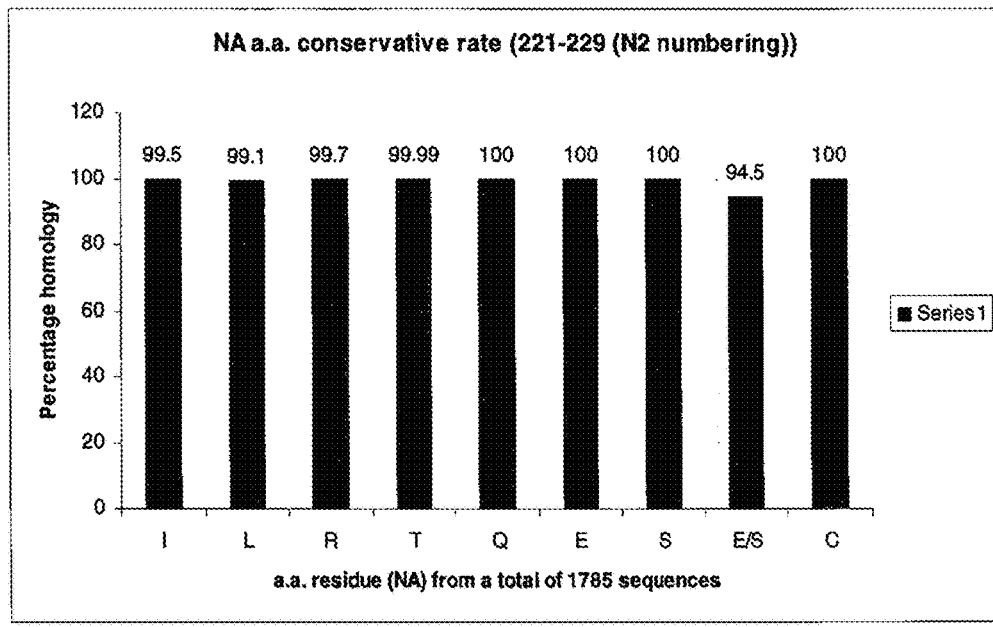
FIG. 1 depicts sequence similarity of influenza A virus neuraminidases. A total of 8813 full length, non redundant influenza type A NA sequences representing any host or HXNX subtype were downloaded from the NCBI influenza Virus resource database, including Pandemic (H1N1) 2009 viruses, and Flu Project Sequences, Shannon entropy was calculated for each position of amino acid of the identified consensus sequences to determine the degree of variation.
Figure 2:
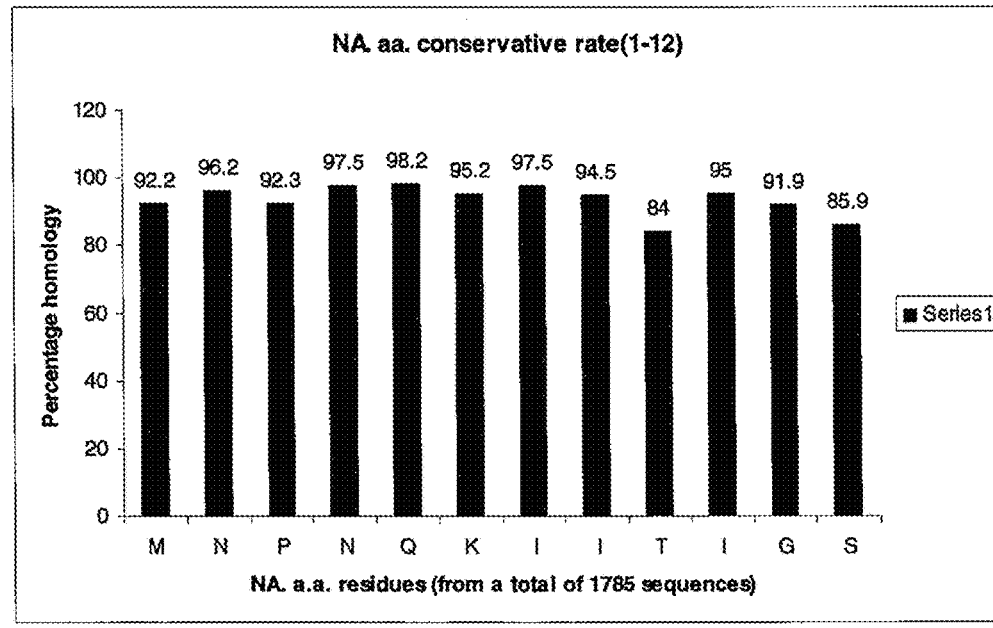
FIG. 2 depicts sequence similarity of influenza A virus neuraminidases. A total of 8813 full length, non redundant influenza type A NA sequences representing any host or HXNX subtype were downloaded from the NCBI influenza Virus resource database, including Pandemic (H1N1) 2009 viruses, and Flu Project Sequences, Shannon entropy was calculated for each position of amino acid of the identified consensus sequences to determine the degree of variation.
Figure 3:
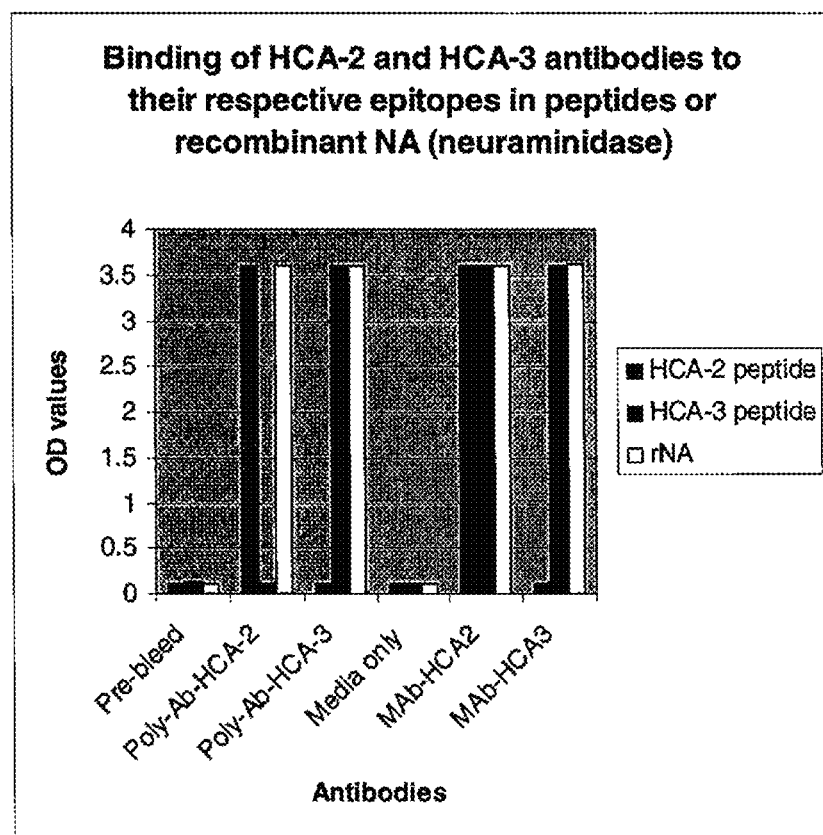
FIG. 3 depicts binding of Mono-specific and monoclonal antibodies to the HCA-2 and HCA-3 epitopes in direct ELISA. HCA-2 or HCA-3 free peptides, GST-peptide or recombinant NA (rNA) were coated, respectively on 96-well plates, following by reaction with the antibodies and $2^{nd}$ goat anti-rabbit IgG peroxidise conjugates. The left side of the figure represents the reactions with non-specific polyclonal antibodies and their pre-bleed controls while the right side of the figure describes the reactions with the monoclonal antibodies (MAbs) derived from the hybridoma supernatants and their culture media controls. The data shows that HCA-2 or HCA-3 mono-specific antibodies (1:4000 dilution) or MAbs (undiluted hybridoma supernatants) bind to their respective epitopes in the free peptides, GST-peptides or rNA. Same results were obtained from affinity-purified antibodies.
Figure 4:
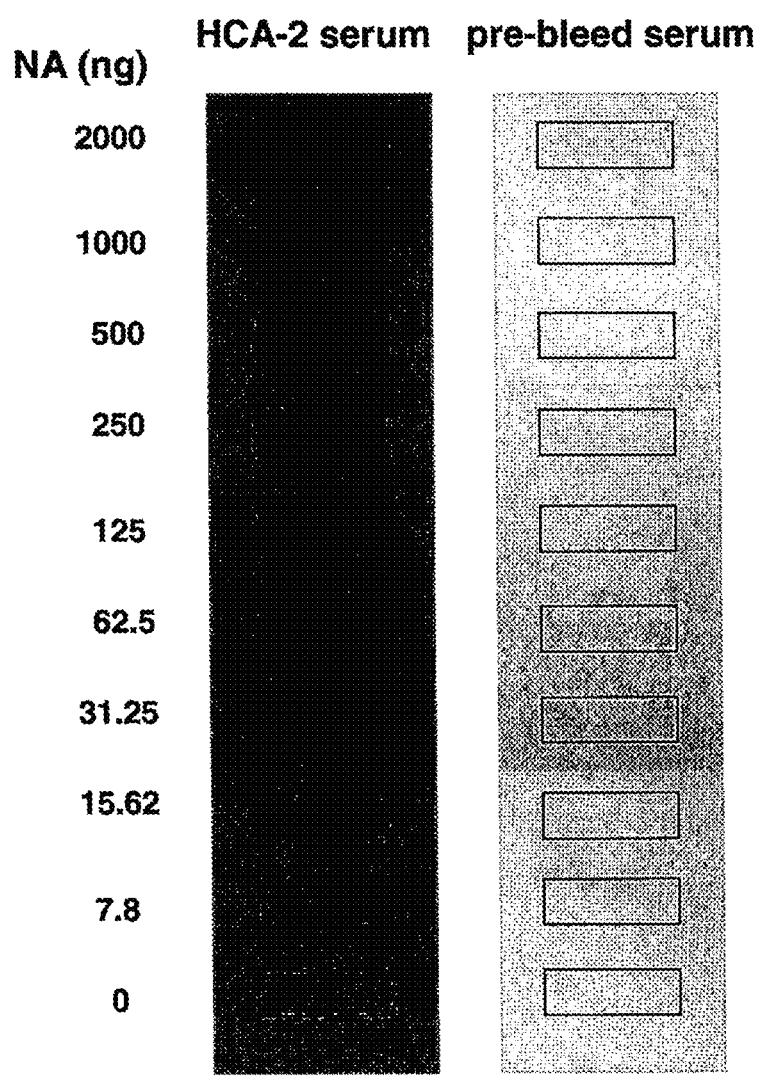
FIG. 4. Quantitative detection of NA using antibodies against NA. The NA antigens were serially diluted in PBS-containing 0.01% Zwittergent (final concentration) and blotted onto PVDF membrane. The membrane is then incubated with the universal antibodies HCA-2 Monoclonal antibodies, followed by detection with anti-rabbit IgG peroxidase conjugate. Slot blot was conducted as described (Li C. et al. 2010).
Figure 5:
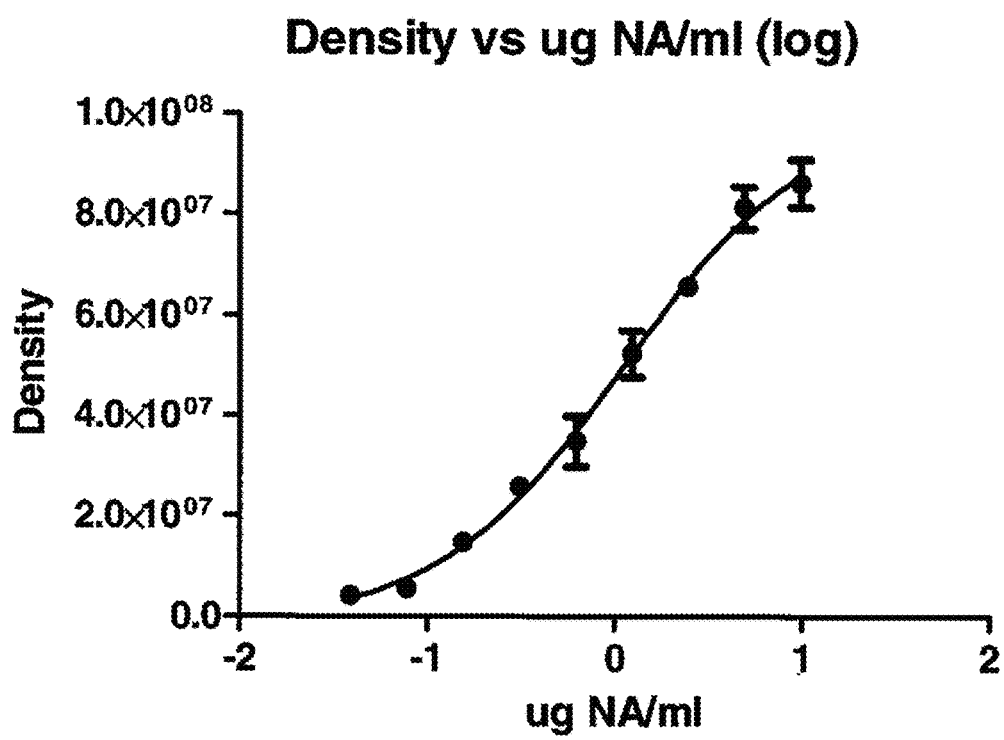
FIG. 5. Standard curve for the quantification of NA by HCA-2. The currently accepted 4-parameter logistic (4-PL) model was employed for the calibration curve fitting in the immunoassays as described (Chun et al 2008) showing that there is a relationship between the amount of signal and the amount of protein. Therefore, antibodies to HCA-2 can be used as a quantitative detection method for detection of NA.
Figure 6:
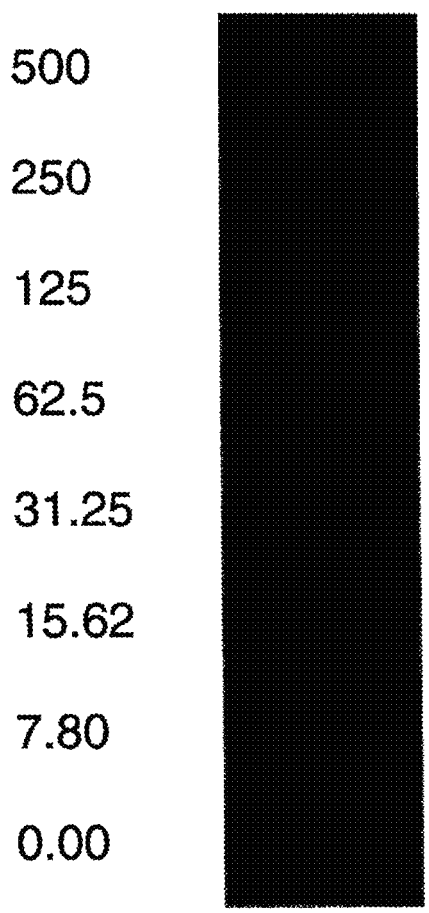
FIG. 6. Quantitative detection of NA using antibodies against NA. The NA antigens were serially diluted in PBS-containing 0.01% Zwittergent (final concentration) and blotted onto PVDF membrane. The membrane is then incubated with the HCA-3 monoclonal antibodies, followed by detection with anti-rabbit IgG peroxidase conjugate. Slot blot was conducted as described (Li C. et al. 2010).
Figure 7:
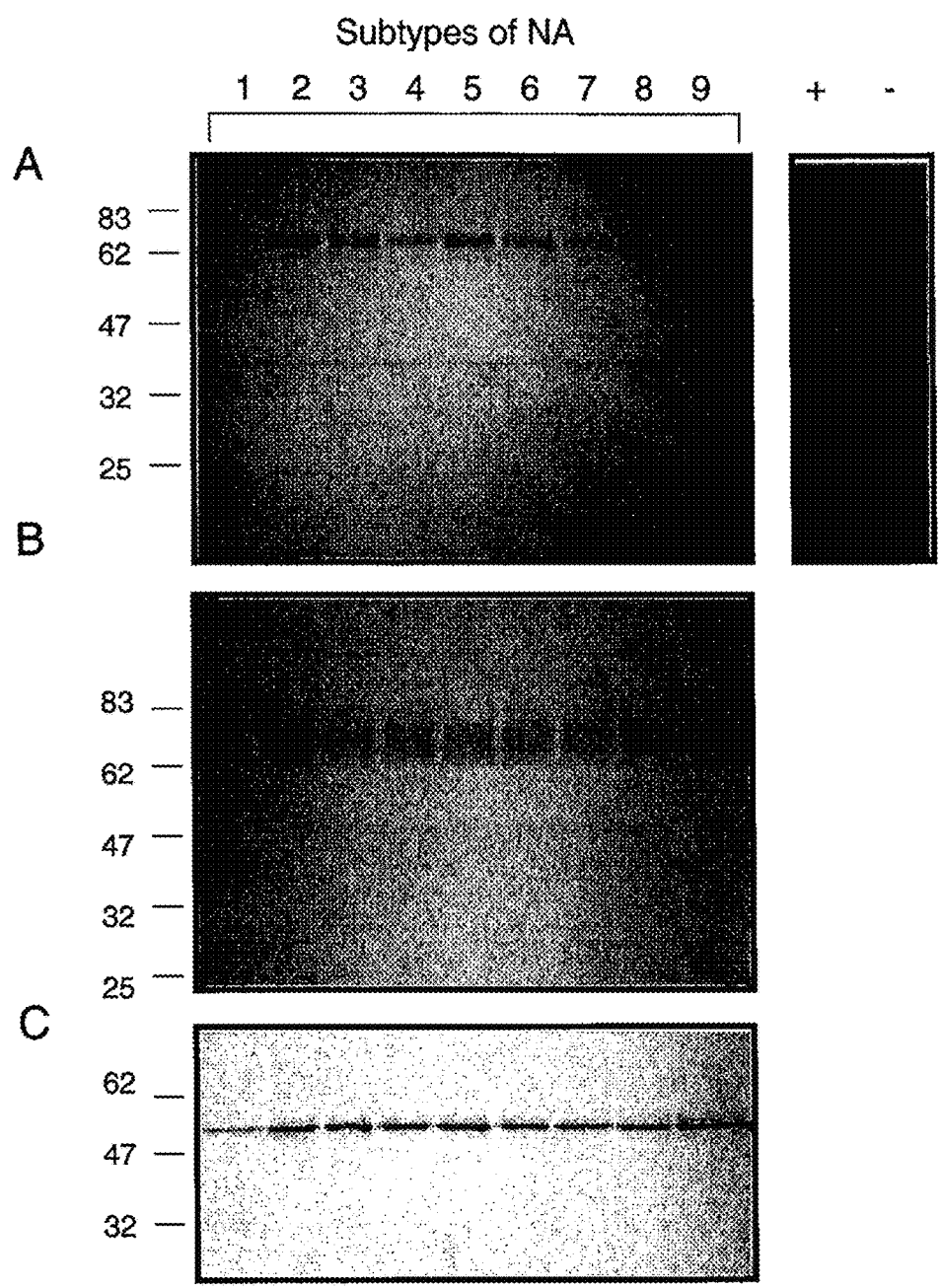
FIG. 7. Binding of HCA-2 and HCA-3 antibodies to 9 subtypes of NA proteins. Allantoic fluids of 9 NA subtypes of influenza viruses propagated in embyronated eggs were fractionated by SDS-PAGE, followed by detection of the NA proteins using the HCA-2 (upper panel) and HCA-3 antibodies (middle panel). Rabbit polyclonal anti-NP proteins of influenza viruses were used as another control (lower gel panel). "+" represents allantotic fluids spiked with rNA or A/New Caledonia/20/99 reacting with the corresponding anti-NA antisera as positive control while the negative controls (−) were allantoic fluids from un-infected eggs.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

The neuraminidases of influenza type viruses play important roles in viral replication by facilitating the release of viral particles from the infected cells. Neuraminidase specific-antibodies alone have been reported to protect animals from lethal challenge and therefore are an important component of an effective influenza vaccine. However, the amount of neuraminidase in current vaccines is typically not determined because of a lack of appropriate reagents, methods and international references standards. Thus, a simple and accurate method capable of quantifying neuraminidase would be useful for better quality control of influenza vaccines.

Antigenic drifting and shifting of the influenza A viruses have presented to the scientific community a daunting challenge in terms of epidemiological monitoring, vaccine development and quality control. We have now generated and characterized antibodies against the most conserved region in the neuraminidase of influenza A viruses. Bioinformatics analyses of all available neuraminidase (NA) sequences from public domain revealed two stretches of amino acids comprised of ILRTQES(E/S)C (SEQ ID NO: 1) which is found at amino acids 223-231 and MNPNQKIIT-IGS (SEQ ID NO: 2) which is found at the N-terminus of NA. As will be appreciated by one of skill in the art, the peptide as set forth is SEQ ID No. 1 can also be expressed as ILRTQESEC (SEQ ID NO: 3) and ILRTQESSC(SEQ ID NO: 4). These regions were found to be present in all viral strains with minor substitutions.

As discussed herein, in one aspect of the invention, there is provided a composition comprising an influenza neuramidase peptide consisting of the amino acid sequence as set forth in SEQ ID No. 1 or SEQ ID No. 2 attached to a first end of a spacer, said spacer being attached at a second end thereof to a carrier protein. Preferably, the neuramidase peptide is attached at its C terminus to the spacer.

As will be appreciated by one of skill in the art, any suitable spacer may be used, for example, but by no means limited to amino acids, peptides, phosphoramidite, ϵ-aminohexanoic acid and 6-aminocaproic acid. In a preferred embodiment, the spacer is 6-aminocaproic acid.

The carrier protein may be any suitable carrier protein known in the art. As will be well known to those of skill in the art such carrier proteins are routinely used for 'presenting' antigens and/or epitopes for eliciting an immune response. As such, the selection of carrier protein depends largely on the intended use and is well within routine skill in the art and does not require undue experimentation. For example, the carrier protein may be selected from the group consisting of keyhole limpet hemocyanin (KLH), bovine serum albumin (BSA), rabbit serum albumin (RSA), ovalbumin (OVA), thyroglobulin (THY) and human gamma globulin (HGG).

As discussed herein, there is also provided a composition comprising an influenza neuramidase peptide consisting of the amino acid sequence as set forth in SEQ ID No. 1 or SEQ ID No. 2 attached to a first end of a spacer, said spacer being attached at a second end thereof to a first end of a linker, said linker being attached at a second end thereof to a carrier protein.

As will be appreciated by one of skill in the art, any suitable linker may be used. In some embodiments, the linker is selected from the group consisting of an amino acid, a peptide of 2-10 amino acids and KKC.

In a preferred embodiment, the linker is KKC and the spacer is 6-aminocaproic acid.

The compositions described herein can also be used to elicit an immune response, for example, as a vaccine, or for the harvesting of antibodies.

For example, in some embodiments, there is provided a method of inducing an immune response in an individual in need of or desirous of such treatment comprising administering to said individual an effective amount of the composition. As will be appreciated by one of skill in the art, 'an effective amount' in this context refers to an amount that is sufficient to induce the desired immune response. It is of note that the effective amount may be administered in one or more doses, for example, as a first initial inoculation followed by one or several additional 'booster' inoculation(s).

In other embodiments, there is provided a method of preparing antibodies against influenza virus neuraminidase comprising inoculating an animal with an effective amount of the composition as described above and after the animal has produced antibodies against said composition, recovering said antibodies from said animal.

In further embodiments, there is provided a method of preparing monoclonal antibodies against influenza virus neuraminidase comprising inoculating an animal with an effective amount of the composition as described above, removing antibody-producing cells from said animal, fusing a respective one of said antibody-producing cells with a respective one of an immortal cell line, thereby producing a respective one hybridoma cell, and selecting for hybridoma cells producing antibodies against said composition.

In other aspects of the invention, there are provided antibodies prepared according to the above methods. As discussed herein, these antibodies may be used in the preparation of a medicament or pharmaceutical composition or as reagents for detecting neuraminidase, as discussed below. As discussed herein and as will be readily apparent to one of skill in the art, such antibodies may be purified or otherwise isolated first using means known in the art.

As will be appreciated by one of skill in the art and as discussed herein, these antibodies may be used for a variety of purposes.

For example, in some embodiments, there is provided a method of determining the potency of an influenza vaccine preparation comprising providing an influenza vaccine preparation to be tested and determining the amount of neuraminidase in said vaccine preparation using antibodies prepared according to one of the methods described above, wherein higher levels of neuraminidase are indicative of a more potent vaccine preparation. As will be appreciated by one of skill in the art and as discussed below, higher levels of neuraminidase are indicative of a more potent vaccine. As such there is not necessarily a 'threshold' level which must be attained but rather it is clear that vaccine preparations containing higher levels of neuraminidase will be more effective than preparations containing lower levers of neuraminidase.

To overcome the weak immunogenicity and insolubility of the peptides, we linked the peptides to 6-aminocaproic acid, followed by the addition of a charged tripeptide (KKC) before its conjugation to the carrier protein KLH (keyhole limpet hemocyanin). We found rabbits generated specific antibodies which recognized NA. The 6-aminocaproic acid spacer was important in inducing antibodies against the peptides.

As discussed below, the specificity of the antibodies were assayed in Western Blot using a wide range of subtypes of influenza A viruses (N1-N9) in crude allantoic fluid preparations. The antibodies were found to bind all NAs with similar intensities while demonstrating no cross-reactivities to egg proteins. Moreover, versatility of the antibodies was demonstrated in a variety of immunoassays, making them useful reagents for quantitative analyses of seasonal and candidate pandemic influenza vaccines as well as useful research tools in laboratory settings. To our knowledge, this is the first report on the generation of antibodies exclusively against the peptide region which can potentially recognize all strains of neuraminidases. The availability of the antibodies enables vaccine developers to quantify the neuaminidase in the vaccine preparations.

Any suitable spacer molecule or combination of spacer molecules may be used. Spacer molecules include, for example, amino acids, peptides, phosphoramidite, ϵ-aminohexanoic acid and 6-aminocaproic acid. In some embodiments, more than one spacer molecule may be used, but care must be taken to avoid solubility problems because some spacers such as 6-aminocaproic acid itself are hydrophobic. The spacer molecule preferably comprises 6-aminocaproic acid.

The carrier protein may be any suitable carrier, for example keyhole limpet hemocyanin (KLH), bovine serum albumin (BSA), rabbit serum albumin (RSA), ovalbumin (OVA), thyroglobulin (THY) and human gamma globulin (HGG). As will be appreciated by one of skill in the art, such carrier proteins are routinely used interchangeably by those of skill in the art in different systems for presenting antigens and/or epitopes for eliciting an immune response. It is noted that substitution of one carrier protein for another, depending on the intended use, is well within ordinary skill in the art and would not require undue experimentation.

In some embodiments, the conserved influenza virus peptide modified with the spacer may be further modified with an appropriate linker. The linker is preferably an amino acid or a peptide having 2-10 amino acids. The linker may facilitate linking the modified peptide to the carrier protein. Generally, the linker links the peptide to the carrier protein. The linker may be chosen to provide further useful properties, for example, to facilitate dissolution of the modified peptide in aqueous solution or to better expose the epitope for antibody generation. In some embodiments, a tripeptide linker, particularly KKC, is preferred.

To raise antibodies against the conserved influenza virus peptide, a mammal may be inoculated with a conjugate of the present invention. Some examples of mammals are rabbit, mouse, rat, hamster, human, deer. The antibodies so raised are preferably purified for further use.

The antibodies may be used for detecting and/or quantifying the presence of influenza neuraminidase (NA) proteins in a sample. The antibodies are useful for detection and/or quantification of NA proteins from many different influenza virus strains, including influenza A and B strains. The universality of the antibodies makes them excellent reagents for determining the potency of influenza vaccines. The antibodies may also be used in earlier stages of seasonal influenza vaccine manufacturing, for example, to estimate presence and/or potency of influenza NA proteins prior to availability of the subtype specific antisera. These would shorten the production of the vaccine and better control the neuraminidase in the manufacturing process. Specifically, neuraminidase can be 'lost' during lengthy manufacturing processes, and the antibodies described herein or made by the methods described herein would allow vaccine manufacturers to know where and how the neuraminidase is lost. The antibodies also permit manufacturing of seasonal influenza vaccine at least 2-3 months ahead of the current schedule, thus greatly facilitating prompt production of the seasonal influenza vaccines and timely release of the vaccines prior to an upcoming flu season.

Numerous attempts have been made in the past by various groups to generate antibodies against the most conserved regions in the NA proteins. Two regions have been identified to be the most conserved regions among all subtypes of influenza A (Jackson et al. 1991; Gerhard et al. 2006). There have been no reports of antibodies that are specific against the highly conserved peptide regions only. Generation of the antibodies against the conserved regions is important because it enables health departments to be well ahead in pandemic flu preparedness. In the event of a pandemic situation, it is currently impossible to have quality control (Q. C.) reagents ready for the lot-release of a pandemic flu vaccine because preparation of the reagents would take at least several months and a pandemic flu could potentially spread globally in a few weeks. However, an assay system based on the present invention can alleviate this problem. Specifically, an assay system based on the present invention can replace the current reagents for the annual (or seasonal) flu assay as well. Currently available prior art reagents for annual flu vaccine lot release (quantitation) are prepared annually and shipped globally by the National Institute for Biological Standards and Control (NIBSC) in the U.K. or the US FDA. There are often problems associated with the variability of the assay among different laboratories and reagents are also often in short supply and cannot meet global needs. However, by having a universal assay system, there will be no need to prepare and ship the reagents each year globally, thus substantially improving the quality control and simplifying the procedure for timely lot release of seasonal (annual) flu vaccines.

By using a bioinformatics approach, we confirmed that two regions were conserved among all subtypes of type A influenza viruses with only minor substitutions. Specifically, peptides most representative of the conserved peptide region were identified (HCA-2 and HCA-3). It is of note that both peptides were relatively hydrophobic, making it extremely difficult to manipulate these peptides and its conjugates, i.e., solubilization, purification, conjugation or immunoassay. In addition, previous attempts using peptides or peptide-conjugates to generate antibodies against the peptide have not been successful (Jackson et al. 1999; Horvath et al. 1998), suggesting these regions are very weakly immunogenic.

To overcome these hurdles, we first linked the identified peptides to a spacer, 6-aminocaproic acid to improve immunogenicity, followed by the addition of a tripeptide KKC to enable solubilization of the peptides and conjugation of the modified peptide to the carrier protein (KLH). Through these modifications, we were successful in generating specific antibodies against the peptides. Although 6-aminocaproic acid as a spacer has been reported by others to link some haptens, e.g., dinitrophenyl, folic acid or polysaccharide, to carrier proteins (Scott et al, 1984; Das Sarma et al. 1995; Okawa et al. 1992), the use of the spacer has not been reported for influenza peptides. At this time, it remains unclear as to how the spacer would help the host in generating antibodies against the peptide although it is of note that two spacers might even be better than a single one for some haptens (Scott et al. 1984; Das Sarma et al. 1995; Okawa et al. 1992). While not wishing to be limited to a specific hypothesis or theory, the inventors note that it is likely that the spacer, 6-aminocarproic acid, which comprises 6 carbon elements, is flexible and allows the peptide to be exposed to the surface of the carrier proteins.

The peptides modified and conjugated in our case were found to be sufficient in inducing antibodies against the immunogens (HCA-2-Acp-KKC-KLH or HCA-3-Acp-KKC-KLH). Furthermore, we found the antibodies were able to bind various recombinant NA proteins (with similar minor substitutions of amino acids to that of the peptides) as well as 9 subtypes of influenza A with remarkable specificity as no cross-reactivity was observed using crude allantoic fluid preparations.

Thus, we here report two peptide regions among all influenza viruses which are highly conserved across all sequences of influenza strains available in the public domain. However, amino acid sequences in the region do have some minor substitutions.

We selected two peptides that are most representative of such variations. As discussed above, to overcome the weak immunogenicity and insolubility of the peptides, we linked the peptides to a 6-aminocaproic acid spacer, a tripeptide (KKC) and conjugated the modified peptide to KLH. The antibodies generated in rabbits demonstrated remarkable binding specificities for diverse strains of influenza A viruses in ELISA and W.B. Collectively, our data indicate that the antibodies described in this report are truly "universal" reagents for the detection of the NA proteins. Not only are they of practical application (vaccine potency testing in the event of a pandemic flu outbreak or as replacement for the current reagents for flu vaccine potency testing) but they are also valuable research tools in laboratory settings.

Further features of the invention will be described or will become apparent in the course of the following detailed description.

Materials and Methods: Preparation of peptides and their conjugates for immunization.

A bioinformatics approach was employed to locate the presence of the conserved regions in the NAs. Sequences from public domains (the NCBI flu resource) were retrieved separately for each subtype. The combined human and avian influenza NA sequences with identical sequences were removed. Next, a separate multiple alignment for each type (A and B) was performed, followed by the extraction of the target region from the full-gene alignment. The Shannon entropy for each position of amino acid of the identified consensus sequences was then calculated to determine the degree of variation. Two peptides were selected. These peptides, from influenza A, ILRTQES(E/S)C (SEQ ID NO: 1) (HCA-2); and MNPNQKIITIGS (SEQ ID NO: 2) (HCA-3) were then modified and conjugated in a procedure described previously with minor modification (Wu et al. 1993; Das Samna et al. 2005). In brief, the peptides were first linked to 6-aminocaproic acid, followed by an addition of a tripeptide (KKC). The modified peptides were then conjugated to the carrier protein KLH using sulfosuccinimidyl-4-(N-maleimidomethyl) cyclohexane-1-carboxylate (Sulfo-SMCC) as cross-linking reagent and purified according to the manufacturer's instruction manual (Fisher Canada, Nepean, ON.). Table 1 summarizes the peptides (HCA-2 and HCA-3) and conjugates thereof used for the generation and characterization of specific antibodies against influenza viruses.

Table 1 depicts the two peptides (HCA-2 and HCA-3) selected. The selection of these peptides was based on bioinformatics analyses of all available influenza NA sequences and represent the most conserved amino acid sequences in the peptide region with minor variations. HA1-C is a control peptide VTGLRNIPSIQSR (SEQ ID NO: 5) located at the C-terminus of NA. Acp denotes 6-aminocaproic acid, an effective spacer to link haptens (dinitrophenyl) to carrier proteins (Scott et al. 1984). KKC represent a tripeptide, which was used here to facilitate solubilization of the carrier-free peptides in aqueous solution for antigen-antibody interaction in ELISA. KLH designates keyhole limpet hemocyanin.

The recombinant NAs were purchased from Proteins Sciences Corporation as described previously (Wang et al. 2006). The trivalent annual influenza vaccines (1-11N1/H3N2/B) were generously provided by the National Institute for the Control of Pharmaceutical and Biological products, Beijing, China.

Production of antibodies against the peptides of NAs. NZW rabbits were obtained from Jackson Laboratory. All animal experiments were conducted in accordance with the Institutional Guidelines and Protocols for Animal Experiments. The animals were immunized subcutaneously with various types of peptide-KLH conjugate mixed with freund complete adjuvant (FCA) at 200 μg per injection, and boosted every three weeks with the same doses of antigen in freund incomplete adjuvant.

The antibodies were purified by using the peptides as ligands in affinity columns in a procedure described previously (Wu et al. 1993). In brief, the antisera were incubated with 5 mL of the peptide on a column for 10 min at room temperature, followed by washing the column at least 5 times with PBS and 0.1% Tween™20. The antibodies were then eluted with acetate buffer (pH 2.0), followed by immediate addition of sodium hydroxide to bring the pH to 7.2 (Wu et al., 1993).

Immunoblotting The specificities of the antibodies were determined in Western Blot using a procedure with minor modifications as described (Casley et al. 2007). Allantoic fluids directly from eggs inoculated with viruses were fractionated on sodium dodecyl sulfate (SDS)-1 0% polyacrylamide gel, followed by transferring the samples to a nitrocellulose filter. The nitrocellulose filter was then blocked with 5% BSA/PBS at 37° C. for 1 hr. Following incubation of filters for 1 hr at 37° C. with rabbit antisera against HA peptides as described above, peroxidase-conjugated goat anti-rabbit immunoglobulin (Ig) G (Sigma, Oakville, Canada) was added for an additional incubation of 1 h at room temperature, followed by chemiluminescent detection (ECL, Amersham Pharmacia Biotech, Piscataway, N.J.). In some cases, dot blotting was used to determine antigen-antibody interaction. The procedure is essentially the same as Western Blot except that the antigens (10 μl) were directly spotted on the nitrocellulose filter.

Quantitative detection of NA using antibodies against NA. The NA antigens were serially diluted in PBS-containing 0.01% Zwittergent (final concentration) and blotted onto PVDF membrane. The membrane is then incubated with the universal antibodies HCA-2 Monoclonal antibodies, followed by detection with anti-rabbit IgG peroxidase conjugate. Slot blot was conducted as described a similar procedure (Li C. et al. 2010). These were then scanned with a densitometer to quantitate. Standard curve for the quantification of NA by HCA-2. The currently accepted 4-parameter logistic (4-PL) model was employed for the calibration curve fitting in the immunoassays as described (Chun et al 2008) showing that there is a relationship between the amount of signal and the amount of protein. Therefore, antibodies to HCA-2 can be used as a quantitative detection method for detection of NA Results: Selection of peptides for the generation of antibodies against diverse strains of influenza viruses Following a comprehensive analysis of the public database, the most conserved sequences were determined to be the amino terminus of the NA and amino acids 221-231 (N2 numbering), largely agreeing with other investigators (Jackson et al. 1991; Horvath et al. 1998. Bianchi et al. 2005; Gerhard et al. 2006). However, it is of note that there are some minor variations as a result of bioinformatics analyses (see Materials and Methods above). Both peptides were relatively hydrophobic, thus presenting daunting challenge to the subsequent peptide manipulations such as synthesis, purification, conjugation and epitope mapping in immunoassays.

The peptides, HCA-2 (SEQ ID NO: 1) and HCA-3 (SEQ OD NO: 2), were used for peptide modification and conjugation. Towards this end, the peptides were first linked with a spacer (6-aminocaproic acid) to improve immunogenicity (Scott et al. 1984), followed by a tripeptide (KKC) to enable solubilization of the peptide and also provide the cysteine residue necessary for conjugation to the KLH carrier. The peptides or peptide-conjugates were injected into NZW rabbits, followed by boosting every two weeks. Significant antibody response was generated in NZW rabbits against both peptide conjugates. The antibodies generated were IgG antibodies.

Binding specificities of the antibodies to diverse strains of the influenza viruses Experiments were then designed to determine whether the antibodies could bind to diverse strains of influenza strains. To this end, 9 subtypes of influenza viruses available at our institutions were propagated in embryonated eggs. Allantoic fluid samples were used directly without any purification step so that the specificity of antibodies could be determined at the same time. As shown in FIG. 6, the antibodies were found to bind all 9 subtypes. It is of note that the differences of reaction intensities amongst the subtypes were mostly likely due to the different titres of virus in the crude allantoic fluids since the binding intensities with anti-HCA-2 and anti-HCA-3 antibodies were largely consistent with that obtained with other anti-influenza proteins (NP). Moreover, the different mobilities of the NA proteins amongst the influenza subtypes are due to the differences of protein size or processing stages of the NA proteins. Importantly, the antibodies demonstrated remarkable specificity against the influenza NAs as no binding of the antibodies to proteins derived from allantoic fluids were detected. As expected, the antibodies could also detect NA proteins from influenza virus grown in embryonated eggs and purified for the preparation of human vaccines including influenza B (FIG. 3B).

While the preferred embodiments of the invention have been described above, it will be recognized and understood that various modifications may be made therein, and the appended claims are intended to cover all such modifications which may fall within the spirit and scope of the invention.

REFERENCES

The contents of the entirety of each of which are incorporated by this reference.

Bianchi E, et al. Universal influenza B vaccine based on the maturational cleavage site of the hemagglutinin precursor. J Virol. (2005 June); 79(12):7380-8.

Bridges C B, at al. Effectiveness and cost-benefit of influenza vaccination of healthy working adults: A randomized controlled trial. JAMA. (2000 Oct. 4); 284(1 3): 1655-63.

Carrat F and Flahauit A. Influenza vaccine: the challenge of antigenic drift. Vaccine. (2007 September 28); 25(39-40): 6852-62.

Das Sarma J, et al. Antibody to folic acid: increased specificity and sensitivity in ELISA by using epsilon-aminocaproic acid modified BSA as the carrier protein. J Immunol Methods. (1995 Jul. 17); 184(1):1-6.

De Filette M, et al. Universal influenza A vaccine: optimization of M2-based constructs. Virology. (2005 Jun. 20); 337(1): 149-61.

Epstein S L, et al. DNA vaccine expressing conserved influenza virus proteins protective against H5N1 challenge infection in mice. Emerg Infect Dis. (2002 August); 8(8):796-801.

Findlay J W and Dillard R F. Appropriate calibration curve fitting in ligand binding assays. AAPS J. (2007 Jun. 29); 9(2):E260-7.

Fouchier R A, et al. Characterization of a novel influenza A virus hemagglutinin subtype (H16) obtained from blackheaded gulls. J Virol. (2005 March); 79(5):2814-22.

Frace A M, et al. Modified M2 proteins produce heterotypic immunity against influenza A virus. Vaccine. (1999 May 4); 17(18):2237-44.

Fan J, Liang X, at al. Preclinical study of influenza virus A M2 peptide conjugate vaccines in mice, ferrets, and rhesus monkeys. Vaccine. (2004 Aug. 13); 22(23-24): 2993-3003.

Gerhard W, at al. Prospects for universal influenza virus vaccine. Emerg Infect Dis. (2006 April); 12(4):569-74.

Gerhard W. Induction of influenza type A virus-specific resistance by immunization of mice with a synthetic multiple antigenic peptide vaccine that contains ectodomains of matrix protein 2. Vaccine. (2003 Jun. 2); 21(19-20):2616-26.

Horvath A, at al. A hemagglutinin-based multipeptide construct elicits enhanced protective immune response in mice against influenza A virus infection. Immunol Lett. (1998 February); 60(2-3): 127-36.

Jackson D C and Brown L E. A synthetic peptide of influenza virus hemagglutinin as a model antigen and immunogen. Pept Res. (1991 May-June); 4(3):1 14-24.

Jackson D C, at al. The central role played by peptides in the immune response and the design of peptide-based vaccines against infectious diseases and cancer. Curr Drug Targets. (2002 April); 3(2): 175-96.

Neirynck S, at al. A universal influenza A vaccine based on the extracellular domain of the M2 protein. Nat Med. (1999 October); 5(10): 1157-63.

Nestorowicz A, et al. Antibodies elicited by influenza virus hemagglutinin fail to bind to synthetic peptides representing putative antigenic sites. Mol Immunol. (1985 February); 22(2): 145-54.

Poland G A, et al. Influenza vaccines: a review and rationale for use in developed and underdeveloped countries. Vaccine. (2001 Mar. 21); 19(1 7-1 9):221 6-20.

Rohm C, et al. Characterization of a novel influenza hemagglutinin, H15: criteria for determination of influenza A subtypes. Virology. (1996 Mar. 15); 217(2):508-16.

Schoofs P G, et al. Epitopes of an influenza viral peptide recognized by antibody at single amino acid resolution. J Immunol. (1988 Jan. 15); 140(2):61 1-6.

Scott D, et al. Immunogenicity of biotinylated hapten-avidin complexes. Mol Immunol. (1984 November); 2 1(1 1):1055-60.

Simonsen L, et al. Mortality benefits of influenza vaccination in elderly people: an ongoing controversy. Lancet Infect Dis. (2007 October); 7(1 0):658-66.

Treanor J. Influenza vaccine-outmaneuvehng antigenic shift and drift. N Engl J Med. (2004 Jan. 15); 350(3):218-20.

Tomasini B R and Mosher D F. Conformational states of vitronectin: preferential expression of an antigenic epitope when vitronectin is covalently and noncovalently complexed with thrombin-antithrombin Ill or treated with urea. Blood. (1988 September); 72(3):903-12.

Wang K, et al. Expression and purification of an influenza hemagglutinin—one step closer to a recombinant protein-based influenza vaccine. Vaccine. (2006 Mar. 15); 24(12): 2176-85.

World Health Organization. (1980). A revision of the system of nomenclature for influenza viruses: a W.H.O. memorandum. Bull. W. H. O. 58:585-591.

Wood J M, et al. The influence of the host cell on standardisation of influenza vaccine potency. Dev Bid Stand. (1999); 98:183-8; discussion 197.

Wu J, et al. Monoclonal antibody-mediated inhibition of HIV-1 reverse transcriptase polymerase activity. Interaction with a possible deoxynucleoside triphosphate binding domain. J Bid Chem. (1993 May 15); 268(1 4):9980-5.

Zambon M C. Epidemiology and pathogenesis of influenza. J Antimicrob Chemother. (1999 November); 44 Suppl B:3-9.

Tulip W R, Varghese J N, Baker A T, van Donkelaar A, layer W G, Webster R G, Colman P M Refined atomic structures of N9 subtype influenza virus neuraminidase and escape mutants. J Mol. Biol. v221, p. 487-497

Varghese J N, layer W G, Colman P M. Structure of the influenza virus glycoprotein antigen neuraminidase at 2.9 A resolution. Nature. 1983 May 5-11; 303(5912):35-40.

Li C, Jaentschke B, Song Y, Wang J, Cyr T D, Van Domselaar G, He R, Li X. A simple slot blot for the detection of virtually all subtypes of the influenza A viral hemagglutinins using universal antibodies targeting the fusion peptide. Nat Protoc. 2010; 5(1):14-9.

Chun S, Li C, Van Domselaar G, Wang J, Farnsworth A, Cui X, Rode H, Cyr T D, He R, Li X. Universal antibodies and their applications to the quantitative determination of virtually all subtypes of the influenza A viral hemagglutinins. Vaccine. 2008 Nov. 11; 26(48):6068-76.

TABLE 1

| Sequences | | |
|---|---|---|
| SEQ ID NO: 1 | HCA-2 | .NILRTQESEC |
| SEQ ID NO: 2 | HCA-3 | MNPNQKIITIGS |
| SEQ ID NO: 3 | na | NILRTQESSC |

TABLE 2

Shannon entropy values for conserved region AA 221-232 of NA (N2 numbering)

| | AA | # | AA | # | AA | # | AA | # | AA | # | AA | # | AA | # | AA | # | AA | # | AA | # |
|---|---|---|---|---|---|---|---|---|---|---|---|---|---|---|---|---|---|---|---|---|
| 221 | N | 458 | D | 138 | Q | 55 | K | 45 | R | 14 | E | 11 | S | 2 | | | | | | |
| 222 | I | 723 | | | | | | | | | | | | | | | | | | |
| 223 | L | 698 | M | 25 | | | | | | | | | | | | | | | | |
| 224 | R | 723 | | | | | | | | | | | | | | | | | | |
| 225 | T | 723 | | | | | | | | | | | | | | | | | | |
| 226 | Q | 722 | E | 1 | | | | | | | | | | | | | | | | |
| 227 | E | 723 | | | | | | | | | | | | | | | | | | |
| 228 | S | 720 | F | 2 | P | 1 | | | | | | | | | | | | | | |
| 229 | E | 629 | S | 94 | | | | | | | | | | | | | | | | |
| 230 | C | 723 | | | | | | | | | | | | | | | | | | |
| 231 | V | 428 | A | 155 | Q | 71 | T | 67 | S | 1 | I | 1 | | | | | | | | |
| 232 | C | 723 | | | | | | | | | | | | | | | | | | |
| 233 | I | 378 | V | 141 | H | 114 | M | 56 | Q | 24 | L | 8 | T | 1 | Y | 1 | | | | |
| 234 | N | 498 | D | 80 | K | 68 | Q | 48 | S | 10 | G | 10 | Y | 4 | R | 3 | E | 1 | H | 1 |

TABLE 3

Shannon entropy values for conserved region AA 1-12 of NA

| | AA | # | AA | # | AA | # | AA | # | AA | # | AA | # | AA | # | AA | # | AA | # |
|---|---|---|---|---|---|---|---|---|---|---|---|---|---|---|---|---|---|---|---|
| 1 | M | 639 | — | 84 | | | | | | | | | | | | | | |
| 2 | N | 644 | — | 76 | D | 1 | K | 1 | G | 1 | | | | | | | | |
| 3 | P | 639 | — | 73 | T | 10 | A | 1 | | | | | | | | | | |
| 4 | N | 654 | — | 66 | Q | 1 | T | 1 | I | 1 | | | | | | | | |
| 5 | Q | 655 | — | 60 | K | 5 | H | 1 | P | 1 | L | 1 | | | | | | |
| 6 | K | 654 | — | 49 | R | 19 | E | 1 | | | | | | | | | | |
| 7 | I | 646 | — | 44 | L | 33 | | | | | | | | | | | | |
| 8 | I | 614 | — | 35 | F | 32 | L | 32 | T | 7 | M | 3 | | | | | | |
| 9 | T | 542 | C | 79 | A | 66 | — | 28 | I | 7 | N | 1 | | | | | | |
| 10 | I | 623 | L | 33 | T | 32 | — | 24 | S | 6 | V | 2 | N | 1 | Y | 1 | M | 1 |
| 11 | G | 590 | S | 119 | — | 12 | W | 1 | P | 1 | | | | | | | | |
| 12 | S | 517 | A | 85 | V | 64 | G | 32 | T | 11 | — | 9 | F | 4 | I | 1 | | |
| 13 | V | 386 | I | 218 | T | 83 | A | 27 | — | 6 | L | 3 | | | | | | |

The invention claimed is:

1. A composition comprising an influenza neuramidase peptide consisting of the amino acid sequence as set forth in SEQ ID No. 1 or SEQ ID No. 2 attached to the first end of a spacer, a tripeptide linker KKC connected to the second end of the spacer and a carrier protein connected to the tripeptide linker.

2. The composition according to claim 1 wherein the spacer is selected from the group consisting of amino acids, peptides, phosphoramidite, ε-aminohexanoic acid and 6-aminocaproic acid.

3. The composition according to claim 1 wherein the carrier protein is selected from the group consisting of keyhole limpet hemocyanin (KLH), bovine serum albumin (BSA), rabbit serum albumin (RSA), ovalbumin (OVA), thyroglobulin (THY) and human gamma globulin (HGG).

4. The composition according to claim 1 wherein the spacer is 6-aminocaproic acid.

5. A composition consisting of an influenza neuramidase peptide consisting of the amino acid sequence as set forth in SEQ ID No. 1 or SEQ ID No. 2 attached to the first end of a spacer, a tripeptide linker KKC connected to the second end of the spacer, and a carrier protein connected to the tripeptide linker.

6. The composition according to claim 5 wherein the carrier protein is selected from the group consisting of keyhole limpet hemocyanin (KLH), bovine serum albumin (BSA), rabbit serum albumin (RSA), ovalbumin (OVA), thyroglobulin (THY) and human gamma globulin (HGG).

7. The composition according to claim 5 wherein the spacer is 6-aminocaproic acid.

* * * * *

SEQUENCE LISTING

<160> NUMBER OF SEQ ID NOS: 5

<210> SEQ ID NO 1
<211> LENGTH: 9
<212> TYPE: PRT
<213> ORGANISM: Influenza virus
<220> FEATURE:
<221> NAME/KEY: MISC_FEATURE
<222> LOCATION: (8)..(8)
<223> OTHER INFORMATION: E or S

<400> SEQUENCE: 1

Ile Leu Arg Thr Gln Glu Ser Xaa Cys
1               5

<210> SEQ ID NO 2
<211> LENGTH: 12
<212> TYPE: PRT
<213> ORGANISM: Influenza virus

<400> SEQUENCE: 2

Met Asn Pro Asn Gln Lys Ile Ile Thr Ile Gly Ser
1               5                   10

<210> SEQ ID NO 3
<211> LENGTH: 9
<212> TYPE: PRT
<213> ORGANISM: Influenza virus

```
<400> SEQUENCE: 3

Ile Leu Arg Thr Gln Glu Ser Glu Cys
1               5

<210> SEQ ID NO 4
<211> LENGTH: 9
<212> TYPE: PRT
<213> ORGANISM: Influenza virus

<400> SEQUENCE: 4

Ile Leu Arg Thr Gln Glu Ser Ser Cys
1               5

<210> SEQ ID NO 5
<211> LENGTH: 13
<212> TYPE: PRT
<213> ORGANISM: Influenza virus

<400> SEQUENCE: 5

Val Thr Gly Leu Arg Asn Ile Pro Ser Ile Gln Ser Arg
1               5                   10
```